(12) United States Patent
Shih et al.

(10) Patent No.: US 12,084,479 B2
(45) Date of Patent: Sep. 10, 2024

(54) MODIFIED ANTIMICROBIAL PEPTIDE DERIVED FROM AN ARGININE-RICH DOMAIN

(71) Applicant: Academia Sinica, Taipei (TW)

(72) Inventors: Chiaho Shih, Taipei (TW); Heng-Li Chen, Taipei (TW); Pei-Yi Su, Taipei (TW)

(73) Assignee: Academia Sinica, Taipei (TW)

( * ) Notice: Subject to any disclaimer, the term of this patent is extended or adjusted under 35 U.S.C. 154(b) by 561 days.

(21) Appl. No.: 16/932,372

(22) Filed: Jul. 17, 2020

(65) Prior Publication Data

US 2021/0101939 A1 Apr. 8, 2021

Related U.S. Application Data

(63) Continuation of application No. 16/303,464, filed as application No. PCT/US2017/034489 on May 25, 2017, now abandoned.

(60) Provisional application No. 62/342,415, filed on May 27, 2016.

(51) Int. Cl.
| | |
|---|---|
| *C07K 14/005* | (2006.01) |
| *A01N 37/46* | (2006.01) |
| *A01N 63/50* | (2020.01) |
| *A61K 38/00* | (2006.01) |
| *A61P 31/04* | (2006.01) |
| *C07K 7/08* | (2006.01) |

(52) U.S. Cl.
CPC ............ *C07K 14/005* (2013.01); *A01N 37/46* (2013.01); *A01N 63/50* (2020.01); *A61P 31/04* (2018.01); *C07K 7/08* (2013.01); *A61K 38/00* (2013.01); *C12N 2730/10122* (2013.01); *C12N 2730/10133* (2013.01)

(58) Field of Classification Search
None
See application file for complete search history.

(56) References Cited

U.S. PATENT DOCUMENTS

| | | | |
|---|---|---|---|
| 6,060,595 A | 5/2000 | Scaglioni et al. | |
| 2003/0105006 A1 | 6/2003 | Mann | |
| 2016/0002300 A1 | 1/2016 | Shih et al. | |

FOREIGN PATENT DOCUMENTS

| | | |
|---|---|---|
| CN | 105101796 A | 11/2015 |
| CU | 01P101-WO | 3/2011 |
| WO | WO-2004/050883 A2 | 6/2004 |
| WO | WO-2014124047 A1 | 8/2014 |

OTHER PUBLICATIONS (<https://www.uniprot.org/uniprotkb/A0A165YEV4/entry> accessed Dec. 17, 2022).*
CU01P101WO-kalen et al.*
Chen et al "Adding a C-Terminal Cysteine (CTC) Can Enhance the Bactericidal Activity of Three Different Antimicrobial Peptides" Frontiers in Microbiology vol. 9, pp. 1-9, 2018.
Mitchell et al "Polyarginine Enters Cells More Efficiently Than Other Polycationic Homopolymers" The Journal of Peptide Research vol. 56, pp. 318-325, 2000.
Akbar et al "Strong and Multi-Antigen Specific Immunity by Hepatitis B Core Antigen (HBcAg)-Based Vaccines in a Murine Model of Chronic Hepatitis B: HBcAg is a Candidate for Therapeutic Vaccine Against Hepatitis B Virus" Antiviral Research vol. 96, pp. 59-64, 2012.
Albada et al "Modulating the Activity of Short Arginine-Tryptophan Containing Antibacterial Peptides with N-Terminal Metallocenoyl Groups" Beilstein Journal of Organic Chemistry vol. 8, pp. 1753-1764, 2012.
Brandenburg et al "Antimicrobial Peptides: Multifunctional Drugs for Different Applications" Polymers vol. 4, pp. 539-560, 2012.
Chen et al ."Identification of a Novel Antimicrobial Peptide from Human Hepatitis B Virus Core Protein Arginine-Rich Domain (ARD)" Pathogens vol. 9, pp. 1-16.
Chen et al ."Improvement of In Vivo Antimicrobial Activity of HBcARD Peptides by D-Arginine Replacement" Applied Microbiology and Biotechnology vol. 100, pp. 9125-9132, 2016.
Chu et al "Nucleic Acid Chaperone Activity Associated with the Arginine-Rich Domain of Human Hepatitis B Virus Core Protein" Journal of Virology vol. 88, pp. 2530-2543, 2014.
Fee et al "Protein PEGylation: An Overview of Chemistry and Process Consideration" EPR vol. 1, 2010.
Hamamoto et al "Antimicrobial Activity and Stability of Proteolysis of Small Linear Cationic Peptides with D-Amino Acid Substitutions" Microbiology and Immunology vol. 46, pp. 741-749, 2002.
Isidro-Llobet et al."Amino-Acid Protecting Groups" Chemistry Review vol. 109, pp. 2455-2504, 2009.
Jung et al ."C-Terminal Substitution of HBV Core Proteins with Those from DHBV Reveals that Arginine-Rich [167]RRRSQSPRR[175] Domain is Critical for HBV Replication" One vol. 7, pp. 1-14, 2014.
Li et al "Nuclear Export and Import of Human Hepatitis B Virus Capsid Protein and Particles" PLOS Pathogens vol. 6, pp. 1-17, 2010.
Merck Manual (https://www.merckmanuals.com/home/skin-disorders/fungal-skin-infections/overview-of-fungal-skin-infections accessed Feb. 19, 2019).
Merck Manual (https://www.merckmanuals.com/professional/infectious-diseases/viruses/overview-of-viruses accessed Feb. 19, 2019).

(Continued)

*Primary Examiner* — Julie Ha
*Assistant Examiner* — Tara L Martinez
(74) *Attorney, Agent, or Firm* — Morse, Barnes-Brown & Pendleton, P.C.; Jeannie Wu

(57) ABSTRACT

An antimicrobial peptide, the peptide comprising 2 to 20 variable domains, each variable domain is a sequence of 2 to 20 consecutive basic amino acids, wherein (a) the variable domains are separated from each other by a variable linker, (b) the variable linker can have 1 to 20 any amino acids other than two or more consecutive basic amino acids, and (c) the peptide has no more than 100 amino acids.

21 Claims, 9 Drawing Sheets

Specification includes a Sequence Listing.

(56) References Cited

OTHER PUBLICATIONS

Miura et al "Basic Peptide Protamine Exerts Antimicrobial Activity Against Periodontopathic Bacteria" Journal of Biomedical Science and Engineering vol. 3, pp. 1069-1072, 2010.
Protective Groups for Peptide Synthesis [online], Peptide Guide 2012 [retrieved on May 25, 2014]. Retrieved from the internet: http://peptideguide.com/protecting-groups-spps.html, p. 1; p. 1, paragraphs 2-3.
Sun et al ."Developing Process and Activity Mechanism of Protegrin" China Academic Journal vol. 24, pp. 366-269, 2007.
UniprotKB—A0A165YEV4 (Jul. 6, 2016).
Veiga et al "Arginine-Rich Self-Assembling Peptides as Potent Antibacterial Gels" Biomaterials vol. 33, pp. 8907-8916, 2012.

* cited by examiner

FIG. 1 a

|  | I | II | III | IV |  |
|---|---|---|---|---|---|
| Human | TVVRRRG- | -----RSPRRR | TPSPRRRSQSP | RRRRSQS-RE | SXC |
| Woolly monkey | TVVRRR-- | -----RPSGRR | TPSPRRRSQSP | RRRRSQS-PA | SSC |
| Ground squirrel | TVIRRRGS | ARVVRSPRRR | TPSPRRRSQSP | RRR-PQS-PA | SNC |
| Woodchuck | TVIRRRSG | ARASRSPRRR | TPSPRRRSQSP | RRRRSQS-PS | ANC |
| Bat | TIVRRRGG | SRATRSTRRR | TPSPRRRSQSP | RRRRSQSPAS | SNC | b

|  | I | II | III | IV |
|---|---|---|---|---|
| Duck | RKPRGL | EPRRRKVKTT | VVYGRRRSKS | RERRAPTPQR |
| Heron | RKPRGL | EPRRRKVKTT | VVYGRRRSKS | RGRRSSSPQR |
| Parrot | RKPRGL | EPRRRKVKTT | VVYGRRRSKS | RERSSSSPQR |
| Ross's goose | RKPRGL | EPRRRKVKTT | VVYGRRRSKS | RERRAPTPQR |
| Snow goose | RKPRGL | EPRRRKVKTT | VVYGRRRSKS | RERRASSPQR |

FIG. 4
a
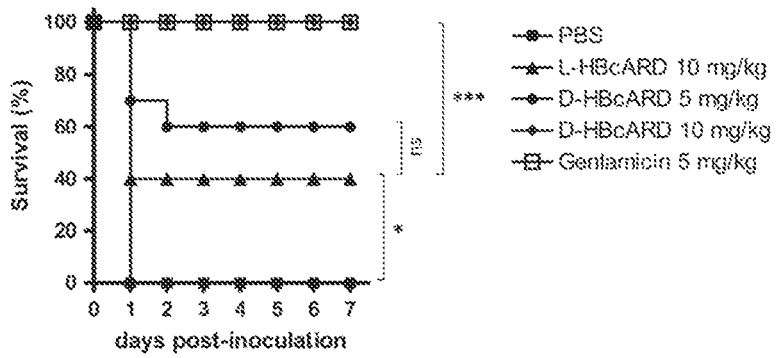
b
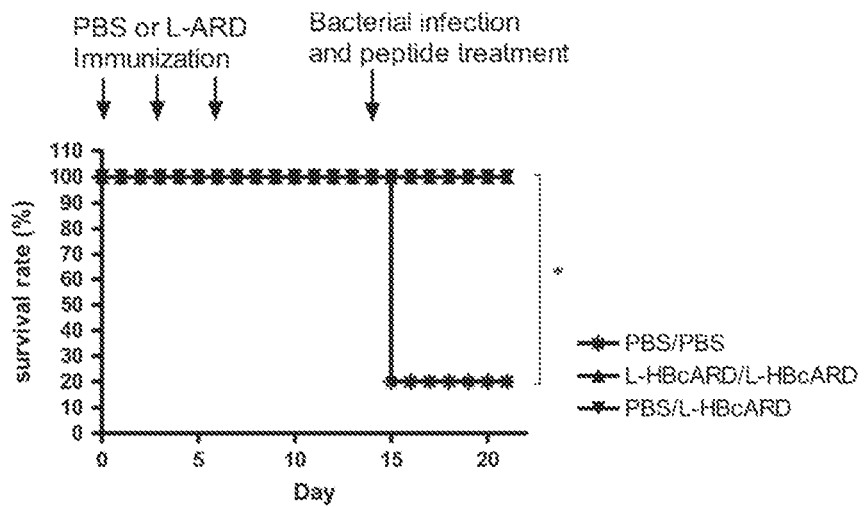
c
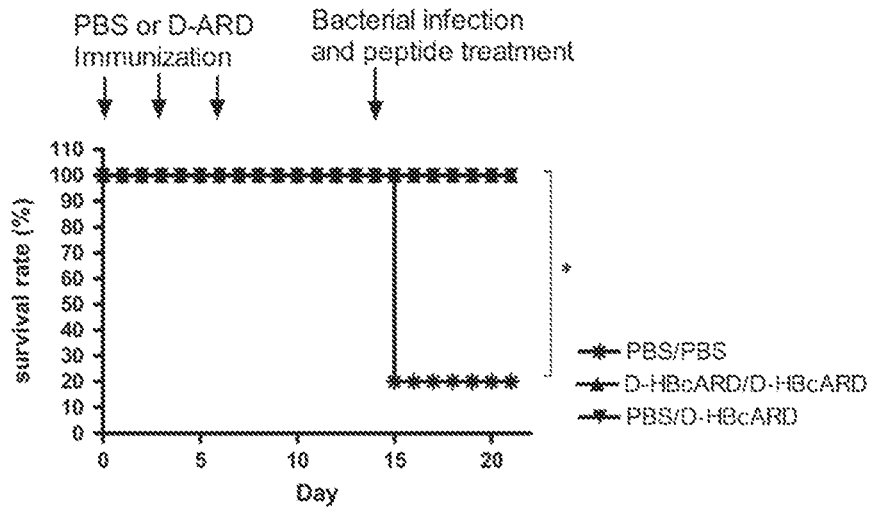

FIG. 7
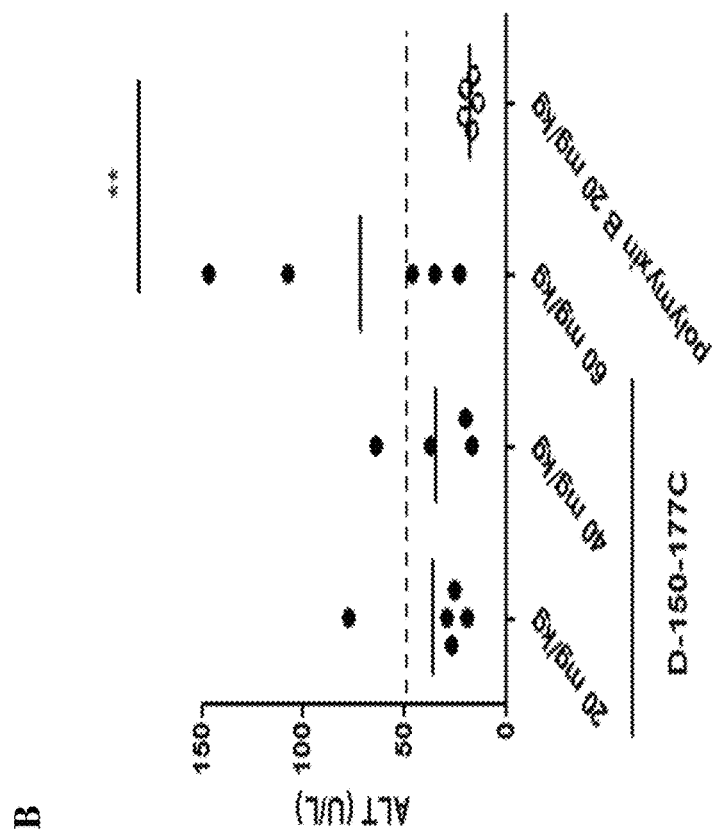
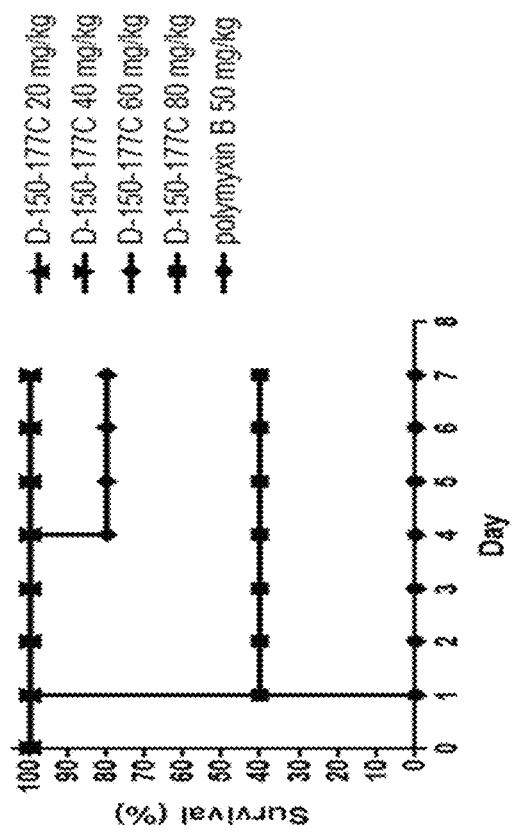

SEQUENCE LISTING

<160> NUMBER OF SEQ ID NOS: 28

<210> SEQ ID NO 1
<211> LENGTH: 16
<212> TYPE: PRT

```
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (4)..(4)
<223> OTHER INFORMATION: Xaa can be any amino acid or absent
<220> FEATURE:
<221> NAME/KEY: MISC_FEATURE
<222> LOCATION: (6)..(6)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (7)..(7)
<223> OTHER INFORMATION: Xaa can be any amino acid or absent
<220> FEATURE:
<221> NAME/KEY: MISC_FEATURE
<222> LOCATION: (9)..(9)
<223> OTHER INFORMATION: Xaa can be any amino acid or absent
<220> FEATURE:
<221> NAME/KEY: MISC_FEATURE
<222> LOCATION: (11)..(11)
<223> OTHER INFORMATION: Xaa can be 2-20 amino acids each selected from
      arginine, lysine, and histidine
<220> FEATURE:
<221> NAME/KEY: MISC_FEATURE
<222> LOCATION: (12)..(12)
<223> OTHER INFORMATION: Xaa can be any amino acid or absent
<220> FEATURE:
<221> NAME/KEY: MISC_FEATURE
<222> LOCATION: (14)..(14)
<223> OTHER INFORMATION: Xaa can be any amino acid or absent
<220> FEATURE:
<221> NAME/KEY: MISC_FEATURE
<222> LOCATION: (16)..(16)
<223> OTHER INFORMATION: Xaa can be 2-20 amino acids each selected from
      arginine, lysine, and histidine

<400> SEQUENCE: 1

Xaa Gly Arg Xaa Pro Xaa Xaa Pro Xaa Pro Xaa Xaa Gln Xaa Pro Xaa
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (4)..(4)
<223> OTHER INFORMATION: Xaa can be any amino acid or absent
<220> FEATURE:
<221> NAME/KEY: MISC_FEATURE
<222> LOCATION: (6)..(6)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (7)..(7)
<223> OTHER INFORMATION: Xaa can be any amino acid or absent
<220> FEATURE:
<221> NAME/KEY: MISC_FEATURE
<222> LOCATION: (9)..(9)
<223> OTHER INFORMATION: Xaa can be any amino acid or absent
<220> FEATURE:
```

```
<221> NAME/KEY: MISC_FEATURE
<222> LOCATION: (11)..(11)
<223> OTHER INFORMATION: Xaa can be 2 to 20 amino acids selected from
      arginine, lysine, and histidine

<400> SEQUENCE: 2

Xaa Gly Arg Xaa Pro Xaa Xaa Pro Xaa Pro Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (2)..(2)
<223> OTHER INFORMATION: Xaa can be any amino acid or absent
<220> FEATURE:
<221> NAME/KEY: MISC_FEATURE
<222> LOCATION: (4)..(4)
<223> OTHER INFORMATION: Xaa can be any amino acid or absent
<220> FEATURE:
<221> NAME/KEY: MISC_FEATURE
<222> LOCATION: (6)..(6)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (7)..(7)
<223> OTHER INFORMATION: Xaa can be any amino acid or absent
<220> FEATURE:
<221> NAME/KEY: MISC_FEATURE
<222> LOCATION: (9)..(9)
<223> OTHER INFORMATION: Xaa can be any amino acid or absent
<220> FEATURE:
<221> NAME/KEY: MISC_FEATURE
<222> LOCATION: (11)..(11)
<223> OTHER INFORMATION: Xaa can be 2 to 20 amino acids selected from
      arginine, lysine, and histidine

<400> SEQUENCE: 3

Xaa Xaa Pro Xaa Pro Xaa Xaa Gln Xaa Pro Xaa
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (4)..(4)
<223> OTHER INFORMATION: Xaa can be any amino acid or absent
<220> FEATURE:
<221> NAME/KEY: MISC_FEATURE
<222> LOCATION: (6)..(6)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (7)..(7)
<223> OTHER INFORMATION: Xaa can be any amino acid or absent
```

-continued

```
<220> FEATURE:
<221> NAME/KEY: MISC_FEATURE
<222> LOCATION: (9)..(9)
<223> OTHER INFORMATION: Xaa can be any amino acid or absent
<220> FEATURE:
<221> NAME/KEY: MISC_FEATURE
<222> LOCATION: (11)..(11)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (12)..(12)
<223> OTHER INFORMATION: Xaa can be any amino acid or absent
<220> FEATURE:
<221> NAME/KEY: MISC_FEATURE
<222> LOCATION: (14)..(14)
<223> OTHER INFORMATION: Xaa can be any amino acid or absent
<220> FEATURE:
<221> NAME/KEY: MISC_FEATURE
<222> LOCATION: (16)..(16)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (17)..(17)
<223> OTHER INFORMATION: Xaa can be any amino acid or absent

<400> SEQUENCE: 4

Xaa Gly Arg Xaa Pro Xaa Xaa Pro Xaa Pro Xaa Xaa Gln Xaa Pro Xaa
1               5                   10                  15

Xaa Cys

<210> SEQ ID NO 5
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (4)..(4)
<223> OTHER INFORMATION: Xaa can be any amino acid or absent
<220> FEATURE:
<221> NAME/KEY: MISC_FEATURE
<222> LOCATION: (6)..(6)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (7)..(7)
<223> OTHER INFORMATION: Xaa can be any amino acid or absent
<220> FEATURE:
<221> NAME/KEY: MISC_FEATURE
<222> LOCATION: (9)..(9)
<223> OTHER INFORMATION: Xaa can be any amino acid or absent
<220> FEATURE:
<221> NAME/KEY: MISC_FEATURE
<222> LOCATION: (11)..(11)
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (12)..(12)
<223> OTHER INFORMATION: Xaa can be any amino acid or absent
<220> FEATURE:
<221> NAME/KEY: MISC_FEATURE
<222> LOCATION: (14)..(14)
<223> OTHER INFORMATION: Xaa can be any amino acid or absent
<220> FEATURE:
<221> NAME/KEY: MISC_FEATURE
<222> LOCATION: (16)..(16)
```

```
<223> OTHER INFORMATION: Xaa can be 2 to 20 amino acids selected from
      arginine, lysine, and histidine
<220> FEATURE:
<221> NAME/KEY: MISC_FEATURE
<222> LOCATION: (17)..(17)
<223> OTHER INFORMATION: Xaa can be any amino acid or absent

<400> SEQUENCE: 5

Xaa Gly Arg Xaa Pro Xaa Xaa Pro Xaa Pro Xaa Xaa Gln Xaa Pro Xaa
1               5                   10                  15

Xaa Gln

<210> SEQ ID NO 6
<211> LENGTH: 37
<212> TYPE: PRT
<213> ORGANISM: Artificial Sequence
<220> FEATURE:
<223> OTHER INFORMATION: Synthetic polypeptide

<400> SEQUENCE: 6

Thr Val Val Arg Arg Gly Arg Ser Pro Arg Arg Thr Pro Ser
1               5                   10                  15

Pro Arg Arg Arg Ser Gln Ser Pro Arg Arg Arg Ser Gln Ser
            20                  25                  30

Arg Glu Ser Gln Cys
            35

<210> SEQ ID NO 7
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 7

Arg Arg Arg Gly Arg Ser Pro Arg Arg Thr Pro Ser Pro Arg Arg
1               5                   10                  15

Arg Arg Ser Gln Ser Pro Arg Arg Arg Ser Cys
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 8

Arg Arg Arg Gly Arg Ser Pro Arg Arg Thr Pro Ser Pro Arg Arg
1               5                   10                  15

Arg Arg Ser Gln Ser Pro Arg Arg Arg Ser Gln
            20                  25

<210> SEQ ID NO 9
<211> LENGTH: 22
<212> TYPE: PRT
<213> ORGANISM: Artificial Sequence
<220> FEATURE:
<223> OTHER INFORMATION: Synthetic polypeptide
```

-continued

```
<400> SEQUENCE: 9

Arg Arg Arg Gly Arg Pro Arg Arg Pro Pro Arg Arg Arg Arg Gln
1               5                   10                  15

Pro Arg Arg Arg Arg Cys
            20

<210> SEQ ID NO 10
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 10

Arg Arg Arg Gly Arg Ser Pro Arg Arg Thr Pro Ser Pro Arg Arg
1               5                   10                  15

Arg Arg Cys

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

Arg Arg Arg Gly Arg Pro Arg Arg Pro Pro Arg Arg Arg Arg Arg Cys
1               5                   10                  15

<210> SEQ ID NO 12
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 12

Arg Arg Arg Thr Pro Ser Pro Arg Arg Arg Ser Gln Ser Pro Arg
1               5                   10                  15

Arg Arg Arg Cys
            20

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Arg Arg Arg Pro Pro Arg Arg Arg Arg Gln Pro Arg Arg Arg Arg Cys
1               5                   10                  15

<210> SEQ ID NO 14
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 14

Arg Arg Arg Gly Arg Ser Pro Arg Arg Thr Pro Ser Pro Arg Arg
1               5                   10                  15
```

-continued

Arg Arg Ser Gln Ser Pro Arg Arg Arg Ser His His His His
            20                  25                  30

His

<210> SEQ ID NO 15
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 15

His His His His His His Arg Arg Arg Gly Arg Ser Pro Arg Arg
1               5                   10                  15

Thr Pro Ser Pro Arg Arg Arg Arg Ser Gln Ser Pro Arg Arg Arg
            20                  25                  30

Ser

<210> SEQ ID NO 16
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 16

Arg Arg Arg Gly Arg Pro Arg Arg Pro Pro Arg Arg Arg Gln
1               5                   10                  15

Pro Arg Arg Arg His His His His His His
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 17

His His His His His His Arg Arg Arg Gly Arg Pro Arg Arg Pro
1               5                   10                  15

Pro Arg Arg Arg Gln Pro Arg Arg Arg
            20                  25

<210> SEQ ID NO 18
<211> LENGTH: 36
<212> TYPE: PRT
<213> ORGANISM: Wooly monkey HepB virus

<400> SEQUENCE: 18

Thr Val Val Arg Arg Arg Pro Ser Gly Arg Arg Thr Pro Ser Pro
1               5                   10                  15

Arg Arg Arg Arg Ser Gln Ser Pro Arg Arg Arg Arg Ser Gln Ser Pro
            20                  25                  30

Ala Ser Ser Cys
        35

<210> SEQ ID NO 19
<211> LENGTH: 41
<212> TYPE: PRT
<213> ORGANISM: Ground squirrel HepB virus

<400> SEQUENCE: 19

Thr Val Ile Arg Arg Gly Ser Ala Arg Val Val Arg Ser Pro Arg
1               5                   10                  15

Arg Arg Thr Pro Ser Pro Arg Arg Arg Ser Gln Ser Pro Arg Arg
            20                  25                  30

Arg Pro Gln Ser Pro Ala Ser Asn Cys
        35                  40

<210> SEQ ID NO 20
<211> LENGTH: 42
<212> TYPE: PRT
<213> ORGANISM: Woodchuck HepB virus

<400> SEQUENCE: 20

Thr Val Ile Arg Arg Gly Gly Ala Arg Ala Ser Arg Ser Pro Arg
1               5                   10                  15

Arg Arg Thr Pro Ser Pro Arg Arg Arg Ser Gln Ser Pro Arg Arg
            20                  25                  30

Arg Arg Ser Gln Ser Pro Ser Ala Asn Cys
        35                  40

<210> SEQ ID NO 21
<211> LENGTH: 43
<212> TYPE: PRT
<213> ORGANISM: Bat HepB virus

<400> SEQUENCE: 21

Thr Ile Val Arg Arg Gly Gly Ser Arg Ala Thr Arg Ser Pro Arg
1               5                   10                  15

Arg Arg Thr Pro Ser Pro Arg Arg Arg Ser Gln Ser Pro Arg Arg
            20                  25                  30

Arg Arg Ser Gln Ser Pro Ala Ser Ser Asn Cys
        35                  40

<210> SEQ ID NO 22
<211> LENGTH: 36
<212> TYPE: PRT
<213> ORGANISM: Duck HepB virus

<400> SEQUENCE: 22

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ala Pro
            20                  25                  30

Thr Pro Gln Arg
        35

<210> SEQ ID NO 23
<211> LENGTH: 36
<212> TYPE: PRT
<213> ORGANISM: Heron HepB virus

<400> SEQUENCE: 23

Arg Lys Pro Arg Gly Leu Glu Pro Arg Arg Lys Val Lys Thr Thr
1               5                   10                  15

Val Val Tyr Gly Arg Arg Arg Ser Lys Ser Arg Gly Arg Arg Ser Ser
            20                  25                  30

Pro Ser Gln Arg
        35

<210> SEQ ID NO 24
<211> LENGTH: 36
<212> TYPE: PRT
<213> ORGANISM: Parrot HepB virus

<400> SEQUENCE: 24

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ser Ser Ser
            20                  25                  30

Ser Pro Gln Arg
        35

<210> SEQ ID NO 25
<211> LENGTH: 36
<212> TYPE: PRT
<213> ORGANISM: Ross' Goose HepB virus

<400> SEQUENCE: 25

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ala Pro
            20                  25                  30

Thr Pro Gln Arg
        35

<210> SEQ ID NO 26
<211> LENGTH: 36
<212> TYPE: PRT
<213> ORGANISM: Snow goose HepB virus

<400> SEQUENCE: 26

Arg Lys Pro Arg Gly Leu Glu Pro Arg Arg Lys Val Lys Thr Thr
1               5                   10                  15

Val Val Tyr Gly Arg Arg Arg Ser Lys Ser Arg Glu Arg Ala Ser
            20                  25                  30

Ser Pro Gln Arg
        35

<210> SEQ ID NO 27
<211> LENGTH: 20
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Xaa can be arginine, lysine, or histidine
<220> FEATURE:
<221> NAME/KEY: MISC_FEATURE
<222> LOCATION: (2)..(2)
<223> OTHER INFORMATION: Xaa can be arginine, lysine, or histidine
<220> FEATURE:
<221> NAME/KEY: MISC_FEATURE
<222> LOCATION: (3)..(3)
<223> OTHER INFORMATION: Xaa can be arginine, lysine, or histidine or
      absent
<220> FEATURE:
<221> NAME/KEY: MISC_FEATURE
<222> LOCATION: (4)..(4)
<223> OTHER INFORMATION: Xaa can be arginine, lysine, or histidine or
      absent
<220> FEATURE:
<221> NAME/KEY: MISC_FEATURE

```
<222> LOCATION: (5)..(5)
<223> OTHER INFORMATION: Xaa can be arginine, lysine, or histidine or
      absent
<220> FEATURE:
<221> NAME/KEY: MISC_FEATURE
<222> LOCATION: (6)..(6)
<223> OTHER INFORMATION: Xaa can be arginine, lysine, or histidine or
      absent
<220> FEATURE:
<221> NAME/KEY: MISC_FEATURE
<222> LOCATION: (7)..(7)
<223> OTHER INFORMATION: Xaa can be arginine, lysine, or histidine or
      absent
<220> FEATURE:
<221> NAME/KEY: MISC_FEATURE
<222> LOCATION: (8)..(8)
<223> OTHER INFORMATION: Xaa can be arginine, lysine, or histidine or
      absent
<220> FEATURE:
<221> NAME/KEY: MISC_FEATURE
<222> LOCATION: (9)..(9)
<223> OTHER INFORMATION: Xaa can be arginine, lysine, or histidine or
      absent
<220> FEATURE:
<221> NAME/KEY: MISC_FEATURE
<222> LOCATION: (10)..(10)
<223> OTHER INFORMATION: Xaa can be arginine, lysine, or histidine or
      absent
<220> FEATURE:
<221> NAME/KEY: MISC_FEATURE
<222> LOCATION: (11)..(11)
<223> OTHER INFORMATION: Xaa can be arginine, lysine, or histidine or
      absent
<220> FEATURE:
<221> NAME/KEY: MISC_FEATURE
<222> LOCATION: (12)..(12)
<223> OTHER INFORMATION: Xaa can be arginine, lysine, or histidine or
      absent
<220> FEATURE:
<221> NAME/KEY: MISC_FEATURE
<222> LOCATION: (13)..(13)
<223> OTHER INFORMATION: Xaa can be arginine, lysine, or histidine or
      absent
<220> FEATURE:
<221> NAME/KEY: MISC_FEATURE
<222> LOCATION: (14)..(14)
<223> OTHER INFORMATION: Xaa can be arginine, lysine, or histidine or
      absent
<220> FEATURE:
<221> NAME/KEY: MISC_FEATURE
<222> LOCATION: (15)..(15)
<223> OTHER INFORMATION: Xaa can be arginine, lysine, or histidine or
      absent
<220> FEATURE:
<221> NAME/KEY: MISC_FEATURE
<222> LOCATION: (16)..(16)
<223> OTHER INFORMATION: Xaa can be arginine, lysine, or histidine or
      absent
<220> FEATURE:
<221> NAME/KEY: MISC_FEATURE
<222> LOCATION: (17)..(17)
<223> OTHER INFORMATION: Xaa can be arginine, lysine, or histidine or
      absent
<220> FEATURE:
<221> NAME/KEY: MISC_FEATURE
<222> LOCATION: (18)..(18)
<223> OTHER INFORMATION: Xaa can be arginine, lysine, or histidine or
      absent
<220> FEATURE:
<221> NAME/KEY: MISC_FEATURE
<222> LOCATION: (19)..(19)
<223> OTHER INFORMATION: Xaa can be arginine, lysine, or histidine or
      absent
<220> FEATURE:
<221> NAME/KEY: MISC_FEATURE
<222> LOCATION: (20)..(20)
<223> OTHER INFORMATION: Xaa can be arginine, lysine, or histidine or
      absent
```

```
<400> SEQUENCE: 27

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 28
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 28

Arg Arg Arg Arg Ser Gln Ser Pro Arg Arg Arg Arg Ser Cys
1               5                   10
```

MODIFIED ANTIMICROBIAL PEPTIDE DERIVED FROM AN ARGININE-RICH DOMAIN

CROSS-REFERENCE TO RELATED APPLICATIONS

The present application is a continuation of copending U.S. patent application Ser. No. 16/303,464, filed Nov. 20, 2018, which was the National Stage of International Application No. PCT/US2017/034489, filed May 25, 2017, which claimed the benefit of U.S. Provisional Application No. 62/342,415, filed May 27, 2016. The contents of these applications are hereby incorporated by reference in their entirety.

BACKGROUND

Antibiotics have been used for the treatment of bacterial infection for more than 60 years. Recently, the increasing number of antibiotics-resistant bacteria has become a major threat to public health. The development of new antibiotics for clinical treatment is an urgent need. Antimicrobial peptides (AMPs) from various species can serve as a defense weapon of the host against pathogenic microbes. Because they can kill bacteria and fungi via different mode of actions, they have been considered as potential candidates to overcome the problem of antibiotic-resistance.

SUMMARY

In one aspect, described herein is an antimicrobial peptide. The peptide contains 2 to 20 variable domains, each variable domain is a sequence of 2 to 20 consecutive basic amino acids, wherein (a) the variable domains are separated from each other by a variable linker, (b) the variable linker can have 1 to 20 any amino acids other than two or more consecutive basic amino acids, and (c) the peptide has no more than 100 amino acids. In one embodiment, peptide has at least 3 or 4 variable domains. The peptide can have a C-terminal cysteine. In some embodiments, at least one of the basic amino acids in the variable domains is an arginine. For example, all of the basic amino acids in each variable domain in the peptide can be arginine residues. Alternatively or in addition, at least one variable domain in the antimicrobial peptide has a lysine. In one embodiment, at least one variable domain has a histidine. The peptide can have a cyclic structure.

At least one of the basic amino acids in the peptide can be a chemically-modified amino acid. In one embodiment, the chemically-modified amino acid is a D-amino acid, e.g., D-arginine. The variable domains and the variable linkers can be derived from the arginine-rich domain of a hepadnavirus core protein (HBcARD). In one embodiment, the HBcARD contains a sequence from residue 147 to the C-terminal residue of a hepadnavirus core protein. Each variable domain in the peptide can have three or four arginine residues and each variable linker in the peptide can have 2 to 4 amino acids. The peptide can exhibit a broad spectrum antimicrobial activity against a gram-positive bacterium, gram-negative bacterium, fungus, parasite, or virus.

In one embodiment, the antimicrobial peptide contains a consensus sequence selected from the group consisting of:
(i) $(X_1)GRX_2P(X_3)X_4PX_5P(X_6)X_7QX_8P(X_9)$ (SEQ ID NO: 1), wherein each of $X_1$, $X_3$, $X_6$, and $X_9$, individually, is a variable domain, and each of $X_2$, $X_4$, $X_5$, $X_7$, and $X_8$, individually, is any amino acid or absent, (ii) $(X_1)GRX_2P(X_3)X_4PX_5P(X_6)$ (SEQ ID NO:2), wherein each of $X_1$, $X_3$, and $X_6$, individually, is a variable domain, and each of $X_2$, $X_4$, and $X_5$, individually, is any amino acid or absent, and (iii) $(X_1)X_2PX_3P(X_4)X_5QX_6P(X_7)$ (SEQ ID NO: 3), wherein each of $X_1$, $X_4$, and $X_7$, individually, is a variable domain, and each of $X_2$, $X_3$, $X_5$, and $X_6$, individually, is any amino acid or absent. Each variable domain is a sequence of 2 to 20 consecutive basic amino acids.

The peptide can have a consensus sequence selected from the group consisting of:

(i)
(SEQ ID NO: 4)
$(X_1)GRX_2P(X_3)X_4PX_5P(X_6)X_7QX_8P(X_9)X_{10}C$,
and (ii)
(SEQ ID NO: 5)
$(X_1)GRX_2P(X_3)X_4PX_5P(X_6)X_7QX_8P(X_9)X_{10}Q$, wherein each of $X_1$, $X_3$, $X_6$, and $X_9$, individually, is a variable domain, and each of $X_2$, $X_4$, $X_5$, $X_7$, $X_8$, and $X_{10}$, individually, is any amino acid or absent.

In one embodiment, the antimicrobial peptide contains a sequence selected from the group consisting of:
(i) TVVRRRGRSPRRRTPSPRRRRSQSPRRRRSQSR-ESQC (SEQ ID NO: 6), in which at least one of the arginine residues is D-arginine, (ii)
(SEQ ID NO: 7)
RRRGRSPRRRTPSPRRRRSQSPRRRRSC, (iii)
(SEQ ID NO: 8)
RRRGRSPRRRTPSPRRRRSQSPRRRRSQ, (iv)
(SEQ ID NO: 9)
RRRGRPRRRPPRRRRQPRRRRC, (v)
(SEQ ID NO: 10)
RRRGRSPRRRTPSPRRRRC, (vi)
(SEQ ID NO: 11)
RRRGRPRRRPPRRRRC, (vii)
(SEQ ID NO: 12)
RRRTPSPRRRRSQSPRRRRC,
and (viii)
(SEQ ID NO: 13)
RRRPPRRRRQPRRRRC.

For example, the antimicrobial peptide can contain the sequence of RRRGRSPRRRTPSPRRRRSQSPRRRRSC (SEQ ID NO: 7), in which each of the arginine residues in the sequence is L-arginine. Alternatively, the peptide can have the sequence of RRRGRSPRRRTPSPRRRR-SQSPRRRRSC (SEQ ID NO: 7), in which at least one of the arginine residues in the sequence is D-arginine.

In one embodiment, the antimicrobial peptide contains the sequence of rRrGRSPrRrTPSPrRrRSQSPrRrRSC (SEQ ID NO: 7), in which R is L-arginine and r is D-arginine. Alternatively, the peptide can contain the sequence of RrR-GRSPrRrTPSPRrRrSQSPRrRrSC (SEQ ID NO: 7), in which R is L-arginine and r is D-arginine.

The antimicrobial peptide can include the sequence of RRRGRPRRRPPRRRRQPRRRRC (SEQ ID NO: 9), in which at least one of the arginine residues (e.g., 20%, 30%, 40%, or 50% of the arginine residues) in the sequence is D-arginine. For example, the sequence can be rRrGRPrRrP-PrRrRQPrRrRC (SEQ ID NO: 9), in which R is L-arginine and r is D-arginine.

In one embodiment, the antimicrobial peptide further contains a non-HBcARD peptide (e.g., an affinity tag, a signal sequence, a ligand, or another antimicrobial peptide or fragment thereof). The non-HBcARD peptide can be a poly-histidine or an analog thereof. In one embodiment, the peptide has a sequence selected from the group consisting of:

(i)
                                       (SEQ ID NO: 14)
RRRGRSPRRRTPSPRRRRSQSPRRRRSHHHHHH, (ii)
                                       (SEQ ID NO: 15)
HHHHHHRRRGRSPRRRTPSPRRRRSQSPRRRRS, (iii)
                                       (SEQ ID NO: 16)
RRRGRPRRRPPRRRRQPRRRRHHHHHH,
and (iv)
                                       (SEQ ID NO: 17)
HHHHHHRRRGRPRRRPPRRRRQPRRRR.

In another aspect, described herein is an antimicrobial peptide conjugate, which contains the antimicrobial peptide disclosed herein and a non-peptide moiety.

In yet another aspect, a pharmaceutical composition is described herein. The composition includes the antimicrobial peptide or the antimicrobial conjugate, and a pharmaceutically acceptable carrier.

Also contemplated herein is a method of treating an infection in a subject in need thereof. The method includes administering to the subject an antimicrobial peptide, an antimicrobial peptide conjugate, or a pharmaceutical composition described herein.

The details of one or more embodiments are set forth in the accompanying drawing and the description below. Other features, objects, and advantages of the embodiments will be apparent from the description and drawing, and from the claims.

BRIEF DESCRIPTION OF DRAWINGS

FIG. 1 includes two sets of sequence alignments of HBcARD domains. (A) HBcARD sequences are highly conserved among human (SEQ ID NO: 6), wooly monkey (SEQ ID NO: 18), ground squirrel (SEQ ID NO: 19), woodchuck (SEQ ID NO: 20), and bat (SEQ ID NO: 21). (B) There are also four positive charge clusters separated in the HBc C-terminus of duck (SEQ ID NO: 22), heron (SEQ ID NO: 23), parrot (SEQ ID NO: 24), Ross's goose (SEQ ID NO: 25) and snow goose hepatitis B virus (SEQ ID NO: 26).

FIG. 4 is a set of graphs showing comparison of in vivo protection activities between L- and D-form HBcARD peptides in a mouse sepsis model infected with S. aureus. (A) Three week-old ICR mice were inoculated with S. aureus ($4 \times 10^6$ CFU/mouse) and i.p. injected with PBS, L-HBcARD, or D-HBcARD at 2 hours post-inoculation. Each group contained ten mice. (B) and (C) Three week-old ICR mice were immunized with L- and D-HBcARD peptides (5 mg/kg), respectively, at day 0, 3 and 6. On day 14, the mice were inoculated with S. aureus ($4 \times 10^6$ CFU/mouse) and i.p. injected with PBS, L-HBcARD or D-HBcARD (10 mg/kg) at 1 hour post-inoculation, respectively. Another group of mice were treated with PBS in parallel as a control. Each group of animals contained five mice. *P<0.05; ***P<0.0001; ns, no significance.

FIG. 7 is a set of graphs showing lower in vivo toxicity of HBcARD peptide D-150-177C in comparison with polymyxin B. At day 0, male ICR mice (5 mice/group) were ip. injected with different doses of D-150-177C peptide (20-80 mg/kg) and polymyxin B (50 mg/kg), respectively. (A) The survival rates of all groups were monitored for 7 days. (B) Serum samples collected from mice treated with D-150-177C and polymyxin B were determined for alanine aminotransferase activity (ALT) at day 1. The dash line represents the mean of ALT value (45 U/L) of ICR mice (Charles River Laboratories).

DETAILED DESCRIPTION

Figure 2:
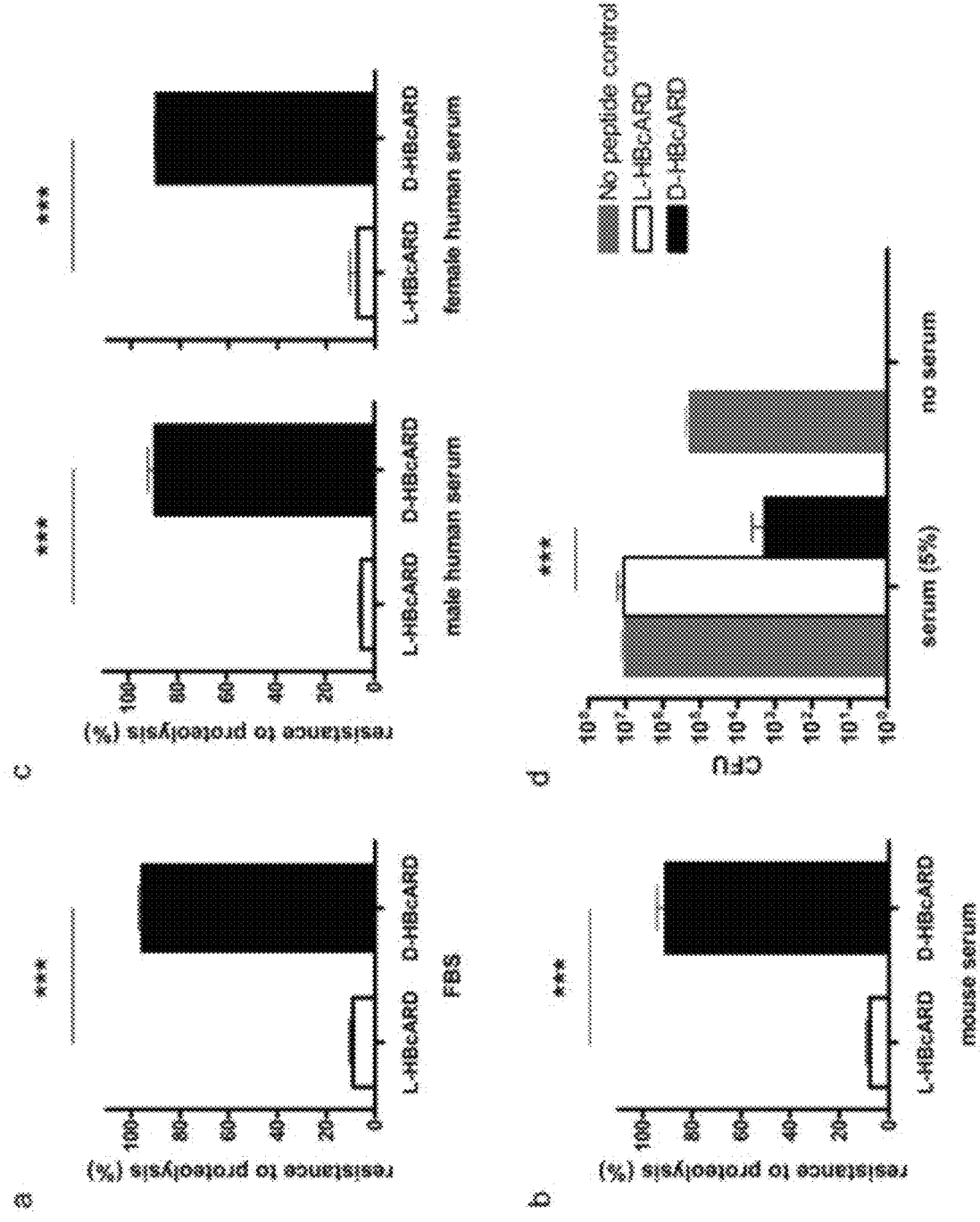
FIG. 2 is a set of graphs showing comparison of serum resistance between L- and D-HBcARD peptides. Peptides (L-HBcARD and D-HBcARD) were incubated with MBC buffer (10 mM sodium phosphate and 50 mM sodium chloride, pH 7.2) containing 5% fetal bovine serum (A), 5% mouse serum (B) or human serum (male and female) (C) at 37° C. for 3 hours. The amounts of peptides were determined using SDS PAGE electrophoresis and green angel staining (D) Peptide D-HBcARD exhibited 10,000-fold higher potency than that of L-HBcARD in MBC assay. Peptides (L-HBcARD and D-HBcARD) were incubated with S. aureus ATCC19636 with or without 5% mouse serum at 37° C. for 3 hours. The antimicrobial activity was determined by colony formation assay. ***P<0.0001.

It was unexpectedly discovered that certain modified peptides derived from an arginine-rich domain of HBV core protein exhibited broad spectrum antimicrobial activities.

Described herein is an antimicrobial peptide. It contains at least two (e.g., 2, 3, 4, 5, 6, 7, 8, 9, 10, 11, 12, 13, 14, 15, 16, 17, 18, 19, or 20) variable domains. The variable domains are in tandem and each separated from another by a variable linker. The antimicrobial peptide can have a maximum length of 100 amino acids (e.g., less than 10, 10, 14, 15, 20, 21, 22, 25, 28, 30, 35, 37, 40, 45, 47, 50, 55, 57, 60, 65, 70, 75, 80, 85, 90, 95, or 100 amino acids). In one embodiment, the peptide has a C-terminal cysteine.

Each of the variable domains, individually, is a sequence of at least two (e.g., 2, 3, 4, 5, 6, 7, 8, 9, 10, 11, 12, 13, 14, 15, 16, 17, 18, 19, or 20) consecutive basic amino acids, e.g., arginine, histidine, and lysine. Each variable domain can contain a sequence of identical basic amino acids or different basic amino acids. For example, the antimicrobial peptides can contain 2 to 20 identical or different variable domains, each being $X_1X_2X_3X_4X_5X_6X_7X_8X_9X_{10}X_{11}X_{12}X_{13}X_{14}X_{15}X_{16}X_{17}X_{18}X_{19}X_{20}$ (SEQ ID NO: 27), wherein each of $X_1$-$X_{20}$, individually, is an arginine, histidine, or lysine (natural or chemically modified) and any of $X_3$-$X_{20}$ can be present or absent. For example, each variable domain can have 2 to 10 basic amino acids.

In one embodiment, at least one variable domain in the peptide consists solely of arginine residues. In another embodiment, all of the variable domains in the peptide contain only arginine residues. Alternatively, the peptide can contain at least one variable domain that has one or more histidine or lysine residues.

Each variable linker has at least one amino acid (e.g., 1, 2, 3, 4, 5, 6, 7, 8, 9, 10, 11, 12, 13, 14, 15, 16, 17, 18, 19, or 20) and can contain any amino acid. It cannot have two or more consecutive basic amino acids.

The term "amino acid" refers to any of the 20 standard amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The term can also refer to a non-standard, non-proteinogenic, or chemically-modified amino acid, or an amino acid analog. An amino acid can be in the L- or D-form stereoisomer.

The term "basic amino acid" refers to arginine, lysine, or histidine, the L- or D-form thereof, or an analog thereof.

Non-standard amino acids include selenocysteine, pyrrolysine, N-formylmethionine, non-proteinogenic amino acids, amino acid analogs, and chemically-modified amino acids. A chemically-modified amino acid or amino acid analog typically has a different side chain from its naturally-occurring counterpart Amino acid analogs and methods of incorporating them into a polypeptide are known in the art. See, e.g., Nguyen et al., Biochemica et Biophysica Acta 1808 (2011), 2297-2303; Knappe, Antimicrobial Agents and Chemotherapy 54(9) 2010, 4003-4005; U.S. Pat. Nos. 7,879,979; 5,972,940; 8,835,162; and US20080199964. Amino acid analogs are also commercially available. Amino acid analogs can be incorporated in the antimicrobial peptide to improve its stability, bioavailability, pharmacokinetics, tissue distribution, safety, tolerability, and/or efficacy.

Any of the antimicrobial peptides described herein can contain one or more residues that are not one of the twenty standard amino acids. In particular, one or more (e.g., 1, 2, 3, 4, 5, 6, 7, 8, 9, 10, 11, 12, 13, 14, 15, 16, 17, 18, 19, 20, 2%, 3%, 5%, 10%, 20%, 25%, 30%, 35%, 40%, 45%, 50%, 55%, 60%, 65%, 70%, 75%, 80%, 85%, 90%, 95%, or 100%) of the basic amino acids in the variable domains or in the entire antimicrobial peptide can be a D-form of natural arginine, lysine, or histidine, or an analog of natural arginine, lysine, or histidine.

The antimicrobial peptide can be derived from the arginine-rich domain of a hepadnavirus core protein (HBcARD). HBcARD refers to a highly conserved arginine-rich C-terminal region of a core protein (HBc). See, FIG. 1. The HBc can be a mammalian HBc or an avian HBc. A mammalian HBc can be human HBc, woolly monkey HBc, ground squirrel HBc, woodchuck HBc, and bat HBc. An avian HBc can be a duck, heron, parrot, Ross's goose, or snow goose HBc. The HBc can be from a hepadnavirus of any genotype.

For example, the antimicrobial peptide can include a fragment of the HBcARD or a variant thereof (e.g., containing one or more amino acid substitutions, deletions, or insertions). The variable domains and the linkers can be derived from an HBcARD. For example, the sequence between any two arginine repeats in an HBcARD or a variant thereof can be used as a linker.

In one embodiment, the antimicrobial peptide contains a consensus sequence selected from the group consisting of:
- (i) $(X_1)GRX_2P(X_3)X_4PX_5P(X_6)X_7QX_8P(X_9)$ (SEQ ID NO: 1), wherein each of $X_1$, $X_3$, $X_6$, and $X_9$, individually, is a variable domain, and each of $X_2$, $X_4$, $X_5$, $X_7$, and $X_8$, individually, is any amino acid or absent,
- (ii) $(X_1)GRX_2P(X_3)X_4PX_5P(X_6)$ (SEQ ID NO:2), wherein each of $X_1$, $X_3$, and $X_6$, individually, is a variable domain, and each of $X_2$, $X_4$, and $X_5$, individually, is any amino acid or absent, and
- (iii) $(X_1)X_2PX_3P(X_4)X_5QX_6P(X_7)$ (SEQ ID NO: 3), wherein each of $X_1$, $X_4$, and $X_7$, individually, is a variable domain, and each of $X_2$, $X_3$, $X_5$, and $X_6$, individually, is any amino acid or absent. Each variable domain is a sequence of 2 to 20 consecutive basic amino acids.

The peptide can have a consensus sequence selected from the group consisting of:

(i)
(SEQ ID NO: 4)
$(X_1)GRX_2P(X_3)X_4PX_5P(X_6)X_7QX_8P(X_9)X_{10}C$,
and (ii)
(SEQ ID NO: 5)
$(X_1)GRX_2P(X_3)X_4PX_5P(X_6)X_7QX_8P(X_9)X_{10}Q$, wherein each of $X_1$, $X_3$, $X_6$, and $X_9$, individually, is a variable domain, and each of $X_2$, $X_4$, $X_5$, $X_7$, $X_8$, and $X_{10}$, individually, is any amino acid or absent.

The antimicrobial peptide can be a fusion or chimeric peptide that further contains a non-HBcARD peptide. A non-HBcARD peptide is not derived from any HBcARD and does not contain at least two variable domains connected by a linker as described above. A non-HBcARD peptide can be a peptide derived from another source (e.g., from a protein other than an HBcARD), an engineered peptide (e.g., another antimicrobial peptide), an affinity tag (e.g., a FLAG, poly-His, Myc, HA, CBP, HBH, or V5 tag), a signal sequence (e.g., a leader sequence or a localization signal), or a ligand (e.g., a receptor ligand).

For example, the antimicrobial peptide can have up to 100 amino acids and contain a sequence selected from the group consisting of:
- (i) TVVRRRGRSPRRRTPSPRRRRSQSPRRRRSQSRESQC (SEQ ID NO: 6), in which at least one of the arginine residues is D-arginine, (ii)
(SEQ ID NO: 7)
RRRGRSPRRRTPSPRRRRSQSPRRRRSC, (iii)
(SEQ ID NO: 8)
RRRGRSPRRRTPSPRRRRSQSPRRRRSQ, -continued (iv)
RRRGRPRRRPPRRRRQPRRRRC, (SEQ ID NO: 9)

(v)
RRRGRSPRRRTPSPRRRRC, (SEQ ID NO: 10)

(vi)
RRRGRPRRRPPRRRRC, (SEQ ID NO: 11)

(vii)
RRRTPSPRRRRSQSPRRRRC, (SEQ ID NO: 12)

(viii)
RRRPPRRRRQPRRRRC. (SEQ ID NO: 13)

(ix)
RRRGRSPRRRTPSPRRRRSQSPRRRRSHHHHHH, (SEQ ID NO: 14)

(x)
HHHHHHRRRGRSPRRRTPSPRRRRSQSPRRRRS, (SEQ ID NO: 15)

(xi)
RRRGRPRRRPPRRRRQPRRRRHHHHHH,
and (SEQ ID NO: 16)

(xii)
HHHHHHRRRGRPRRRPPRRRRQPRRRR. (SEQ ID NO: 17)

As described herein, the antimicrobial peptide can have one or more modified amino acids. For example, in any of the above-described sequences or consensus sequences, one or more of the basic amino acids in the variable domains or in the entire antimicrobial peptide can be a D-form of natural arginine, lysine, or histidine, or an analog of natural arginine, lysine, or histidine.

Any of the above-described sequences or consensus sequences can be at the N- or C-terminus of the antimicrobial peptide.

The antimicrobial peptide described herein can also be conjugated to a non-peptide moiety at the N- or C-terminus to form a peptide conjugate. A non-peptide moiety can be a polymer (e.g., a polyethylene glycol polymer), oligosaccharide, lipid, glycolipid, solid support (e.g., a bead or nanoparticle), small molecule drug, biotin, nucleic acid molecule, antibody, vitamin, carrier protein (e.g., KLH, BSA, or OVA), or detectable label (e.g., fluorescent, radioactive, or enzymatic label). The peptide conjugate also exhibits an antimicrobial activity. Methods of generating peptide conjugates are known in the art.

The antimicrobial peptide or peptide conjugate described herein can be mixed with a pharmaceutically acceptable carrier to form a pharmaceutical composition.

The composition can be formulated with a pharmaceutically acceptable carrier such as a phosphate buffered saline, a bicarbonate solution, and/or an adjuvant. Suitable pharmaceutical carriers and diluents, as well as pharmaceutical necessities for their use, are known in the art. This composition may be prepared as an injectable, liquid solution, emulsion, or another suitable formulation.

An effective amount of the composition described above may be administered by intranasal inhalation, topical application, or parenteral routes, e.g., intravenous injection, subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders.

The above-described composition can be administered to a subject (e.g., a human, another mammal, or a laboratory animal) to treat a microbial infection or to inhibit growth of a microbe in the subject. The composition can be used to treat an infection caused by a Gram-positive or Gram-negative bacteria, fungus, parasite, or virus, e.g., *Pseudomonas aeruginosa, Klebsiella pneumoniae, Shigella dysenteriae, Escherichia coli, Staphylococcus aureus, Acinetobacter baumannii, Clostridium Difficile, Candida, Aspergillus, Blastomyces, Cryptococcus neoformans, Cryptococcus gattii, Coccidioides, Histoplasma, Pneumocystis jirovecii*, ringworm, *Sporothrix, Exserohilum*, or *Cladosporium*.

The specific disclosure below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

Modified Antimicrobial Peptides Derived from Human HBcARD

A novel antimicrobial peptide from human hepatitis B virus (HBV) core protein (HBc) arginine-rich domain (ARD) was previously identified. See Chen et al. (2013), PLoS Pathog 9:e1003425 doi:10.1371/journal.ppat.1003425, and Chen et al., (2016), Appl Microbiol Biotechnol. 100(21): 9125-9132. This HBcARD peptide showed a broad spectrum antimicrobial activity against Gram-negative and Gram-positive bacteria. In our mouse sepsis model, injection of HBcARD peptide at 2 hour postinoculation can protect 40% of *S. aureus*-infected mice from death. See Chen et al. (2013).

The HBcARD peptides are highly conserved in the hepadnaviruses of different species. To improve the antimicrobial efficacy of HBcARD, we compared the sequences and antimicrobial activities of various HBcARD peptides of mammalian, rodent, and avian hepadnaviruses. HBcARD peptide of human hepadnaviruses displayed the strongest antimicrobial activity.

To further improve the potency of our lead compound HBcARD, we tested the antimicrobial activity of each of several HBcARD derivatives, including peptides modified by truncation and D-arginine substitution for L-arginine. See Table 1.

TABLE 1

Sequences of various HBcARD peptides tested for their bactericidal activity

| HBcARD peptide | amino acid sequence |
| --- | --- |
| L-147-183 | TVVRRRGRSPRRRTPSPRRRRSQSPRRRRSQSRESQC (SEQ ID NO: 6) |
| D-147-183 | TVVrrrGrSPrrrTPSPrrrrSQSPrrrrSQSrESQC (SEQ ID NO: 6) |

TABLE 1-continued

Sequences of various HBcARD peptides
tested for their bactericidal activity

| HBcARD peptide | amino acid sequence |
|---|---|
| 150-177C | RRRGRSPRRRTPSPRRRRSQSPRRRRSC (SEQ ID NO: 7) |
| 150-177Q | RRRGRSPRRRTPSPRRRRSQSPRRRRSQ (SEQ ID NO: 8) |
| 150-168C | RRRGRSPRRRTPSPRRRRC (SEQ ID NO: 10) |
| 157-176C | RRRTPSPRRRRSQSPRRRRC (SEQ ID NO: 12) |
| 164-177C | RRRRSQSPRRRRSC (SEQ ID NO: 28) |

TABLE 1-continued

Sequences of various HBcARD peptides
tested for their bactericidal activity

| HBcARD peptide | amino acid sequence |
|---|---|
| D-150-177C | rrrGrSPrrrTPSPrrrrSQSPrrrrSC (SEQ ID NO: 7) |
| DL-150-177C | rRrGRSPrRrTPSPrRrRSQSPrRrRSC (SEQ ID NO: 7) |
| LD-150-177C | RrRGRSPRrRTPSPRrRrSQSPRrRrSC (SEQ ID NO: 7) |
| DL-dST-150-177C | rRrGRPrRrPPrRrRQPrRrRC (SEQ ID NO: 9) |

R: L-arginine;
r: D-arginine

Comparison of Sequences and Antimicrobial Activities of Human and Non-Human HBcARD Peptides By multiple sequence alignment, we compared the sequences of HBcARD peptides of various hepadnaviruses, including human (AAP31571.1), wooly monkey (AAO74859.1), ground squirrel (AAB08031.1), woodchuck (AAA46761.1), bat (AGT17576.1), duck (AAO49490.1), heron (AAA45737.1), parrot (AFY97786.1), Ross's goose (AAR89928.1) and snow goose (AAD22001.1). See FIG. 1.

Similar to the HBcARD peptide of human hepatitis B virus, HBcARD peptides of other mammalian hepadnaviruses (wooly monkey, ground squirrel, woodchuck and bat) contained four clustering arginine-rich domains. While the sequence homology of HBcARD peptides between avian and mammalian hepadnaviruses was low, they both contained four highly positive-charged domains. To compare their respective antimicrobial activities, we determined the minimal bactericidal concentrations of four HBcARD peptides derived from bat, woodchuck, duck and heron hepadnaviruses. The results indicated that peptides derived from bat and woodchuck hepadnaviruses exhibited potent antimicrobial activity comparable to that from human hepatitis B virus. See Table 2. In contrast, peptides derived from avian hepadnaviruses displayed lower antimicrobial activity. Because HBcARD peptides from human HBV is shorter in length (147-183; 37 amino acids), we focused on this peptide in our subsequent modification and optimization experiments.

TABLE 2

Antimicrobial activity of human, bat, woodchuck, duck and heron
HBcARD peptides against Gram-positive and Gram-negative bacteria

| | Minimal bactericidal concentration (mg/L) | | | | |
|---|---|---|---|---|---|
| Bacterial strain[a] | Human HBcARD | Bat HBcARD | Woodchuck HBcARD | Duck HBcARD | Heron HBcARD |
| P. aeruginosa ATCC 9027 | 9.2 | 10 | 9.8 | >70.6 | >69.3 |
| K. pneumoniae ATCC 13884 | 9.2 | 5 | 9.8 | >70.6 | >69.3 |
| E. coli ATCC 25922 | 18.4 | 20 | 19.6 | ND | ND |
| A. baumannii ATCC 17978 | 2.3 | 2.5 | 4.9 | 70.6 | 69.3 |
| S. aureus ATCC 19636 | 18.4 | 20 | 19.6 | ND | ND |

[a]ATCC: American Type Culture Collection;
ND: not detectable

Comparison of Antimicrobial Activity of L- and D-HBcARD Peptides

We used PeptideCutter to predict the potential protease cleavage sites on the HBcARD 147-183 peptide (37-mer). The results showed that more than 70% of the protease cleavage sites were mapped to the arginine residues of HBcARD peptide (data not shown). To improve the peptide stability in the serum, we synthesized a modified peptide, D-HBcARD 147-183 peptide, by D-amino acid replacement, in which all arginine residues were replaced with its D-isomer.

To investigate whether D-arginine substitution will improve the antimicrobial activity, L- and D-HBcARD peptides (37-mer) were tested side-by-side against a wide variety of bacteria, including P. aeruginosa, K. pneumoniae, A. baumannii, E. coli, S. dysenteriae and S. aureus. Relative to the L-HBcARD, the D-HBcARD peptide displayed similar antimicrobial activity against A. baumannii (MBC=2.3-4.6 mg/L), and better antimicrobial activity against P. aeruginosa (MBC=4.6 mg/L), K. pneumoniae (MBC=4.6 mg/L), and S. aureus (MBC=4.6-9.2 mg/L). However, for reasons that remain unclear, the antimicrobial activity of D-HBcARD peptide against E. coli and S. dysenteriae was decreased from 18.4 to 73.6 mg/L. See Table 3.

TABLE 3

Comparison of minimal bactericidal concentration (MBC) between wild type HBcARD 147-183 peptide L-HBcARD and D-HBcARD

| Bacterial strain[a] | Minimal bactericidal concentration (mg/L) | |
|---|---|---|
| | L-HBcARD (37-mer) | D-HBcARD (37-mer) |
| Gram-negative | | |
| P. aeruginosa ATCC 9027 | 9.2 | 4.6 |
| P. aeruginosa ATCC 27853 | 9.2-18.4 | 4.6 |
| K. pneumoniae ATCC 13884 | 9.2 | 4.6 |
| E. coli ATCC 25922 | 18.4 | 73.6 |
| A. baumannii ATCC 17978 | 2.3 | 2.3 |
| A. baumannii ATCC 17978CR[b] | 2.3 | 2.3 |
| A. baumannii ATCC 19606 | 2.3 | 2.3 |
| A. baumannii ATCC 19606CR[b] | 2.3 | 2.3 |
| A. baumannii TCGH 45530[b] | 2.3 | 2.3 |
| A. baumannii TCGH 46709[b] | 4.6 | 4.6 |
| S. dysenteriae Xen27[c] | 18.4 | 73.6 |
| Gram-positive | | |
| S. aureus ATCC 19636 | 18.4 | 9.2 |
| S. aureus ATCC 25923 | 18.4 | 4.6 |
| S. aureus ATCC 29213 | 18.4 | ~4.6 |

[a]ATCC: American Type Culture Collection
[b]Colistin-resistant A. baumannii (Laboratory induced and Clinical isolates from Tzu Chi General Hospital (Chen et al. PLoS Pathog. 2013; 9(6): e1003425.)
[c]Caliper Life Sciences, Inc.

Comparison of Serum Resistance Between L-HBcARD and D-HBcARD

To compare the stability of the 37-mer L- and D-HBcARD peptides against serum protease degradation, we performed a protease resistance assay. After incubation with 5% bovine serum at 37° C. for 3 hours, more than 80% of L-HBcARD peptide was no longer detectable by staining with Green Angel on SDS-PAGE. In contrast, the signal intensity of the D-HBcARD peptide was not reduced under the same condition. See FIG. 2, A. Similar results were obtained, when L-HBcARD was incubated with 5% mouse or human (male and female) sera. See FIGS. 2, B and C. These results suggested that D-HBcARD was more resistant than L-HBcARD to protease digestion of fetal bovine, mouse and human serums.

Furthermore, we determined the in vitro antimicrobial activity of L- and D-HBcARD peptides in the presence of serum. The results showed that both L-HBcARD and D-HBcARD peptides at 18.4 mg/L concentration were able to kill S. aureus in the MBC assay. See FIG. 2, D. Upon the addition of 5% mouse serum, there was a significant difference in the antimicrobial activities between L- and D-HBcARD peptides (P<0.0001). While the treatment with L-HBcARD peptide in the presence of 5% mouse serum produced $10^7$ bacterial colonies, treatment with D-HBcARD peptide produced around $10^3$ colonies. Therefore, our D-HBcARD peptide exhibited higher antimicrobial activity than that of the L-HBcARD peptide in the presence of 5% mouse serum. This observation suggested that D-HBcARD was more stable and resistant to proteolytic degradation.

Hemolytic Activity of D-HBcARD Peptide

Figure 3:
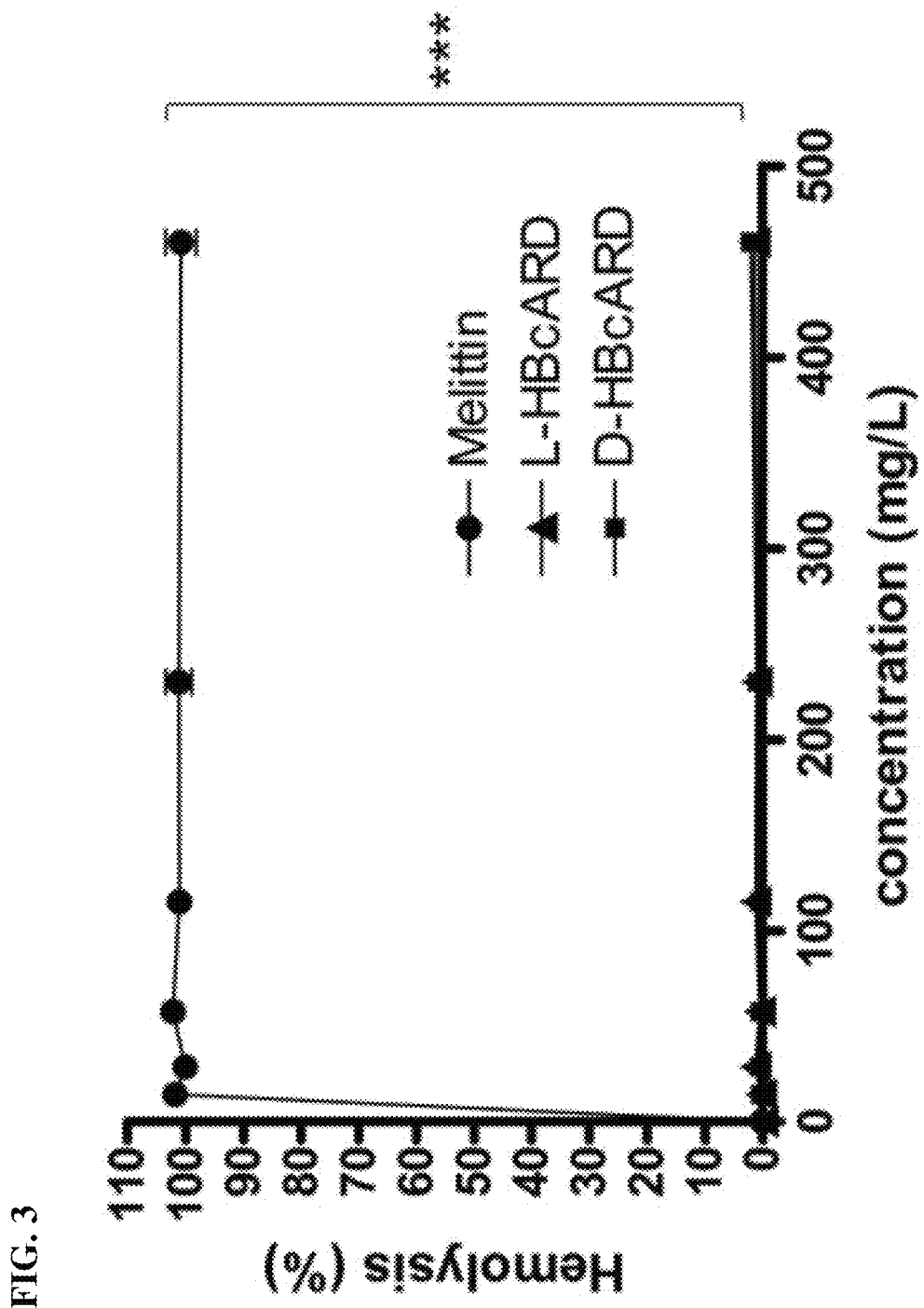
FIG. 3 is a graph showing comparison of hemolytic effect between L- and D-HBcARD peptides. Human red blood cells were incubated with different concentrations of the peptides. Hemolysis is presented as the percentage of Triton X-100-induced hemolysis. ***P<0.0001.

In the hemolysis assay, human RBCs were incubated with serially-diluted doses (0 to 460 mg/L) of D-HBcARD, L-HBcARD, or melittin, at 37° C. for one hour. As shown in FIG. 3, melittin caused 100% hemolysis at the concentration of 8.9 mg/L. In contrast, no hemolytic activity of both D- and L-HBcARD peptides was detected up to 460 mg/L (P<0.0001).

Comparison of In Vivo Protection Efficacies Between L- and D-Form HBcARD Peptides in a Mouse Sepsis Model Infected with S. aureus To investigate the in vivo protection efficacy of the 37-mer L- and D-HBcARD peptides, we performed a mouse sepsis model infected with S. aureus. ICR mice were first i.p. inoculated with S. aureus ($4 \times 10^6$ CFU/mouse), followed by one single i.p. injection of L-HBcARD, D-HBcARD and PBS at two hours post-inoculation, respectively. All mice (n=10) administered with PBS died at day 1. See FIG. 4, A. At 7 days post-inoculation, 40% of mice treated with L-HBcARD (10 mg/kg) survived. See FIG. 4, A. In contrast, D-HBcARD peptide was able to achieve a much higher survival rate (60% for 5 mg/kg dose, and 100% for 10 mg/kg dose). See FIG. 4, A. These results indicated that the in vivo efficacy of HBcARD can be improved by the D-arginine replacement strategy (P<0.0001).

Comparison of the Immunogenicity Between L- and D-Form HBcARD Peptides in a Mouse Sepsis Model Infected with S. aureus To investigate whether repeated treatments with the 37-mer HBcARD peptides may compromise the efficacy by inducing neutralization antibody in vivo, we immunized 3-week old mice three times with L- and D-HBcARD peptides, respectively, prior to bacterial infection. Two weeks after the first immunization, immunized mice were then inoculated with S. aureus, followed by i.p. injection with either L- or D-HBcARD peptides 1 hour post-inoculation. Consistent with our previous report (Chen et al., 2013), L-HBcARD still protected all mice from death, irrespective of the prior immunizations with or without L-HBcARD peptide. See FIG. 4, B. Control mice immunized with PBS and treated with PBS showed a mortality near 80% within 24 hours after bacterial challenge (P<0.05). Seven days post-inoculation, all mice treated with L- and D-HBcARD (10 mg/kg) survived bacterial challenge, irrespective of the prior immunization with or without D-HBcARD. See FIG. 4, C. Therefore, prior immunizations with either D-form or L-form peptides induced no neutralization activity against the in vivo antimicrobial activity of subsequent treatments with HBcARD peptides.

Significance of Terminal Cysteine

We tested the antimicrobial activity of additional HBcARD derivatives. See Table 1. The antimicrobial activities of these peptides were determined by minimal bactericidal concentration (MBC). Unlike the parental peptide HBcARD 147-183 (37-mer) (see Chen et al., 2013), the derivative peptide HBcARD 150-177Q (28-mer) showed no detectable bactericidal activity against S. aureus. See Table 4. To mimic the parental peptide HBcARD 147-183 with a cysteine at the carboxyl terminus, we designed another 28-mer derivative HBcARD 150-177C by replacing the terminal Q (glutamine) residue of HBcARD 150-177Q with a C (cysteine) residue. See Table 1. Interestingly, this Q-to-C substitution effectively rescued the bactericidal activity against S. aureus. See Table 4.

TABLE 4

Minimal bactericidal concentrations (MBC) of modified HBcARD peptides against various Gram-negative and Gram-positive bacteria

| Bacteria strains | MBC (uM) | | | | |
|---|---|---|---|---|---|
| | 150-177C | 150-177Q | 150-168C | 157-176C | 164-177C |
| Gram-negative | | | | | |
| P. aeruginosa ATCC9027 | 2 | — | — | — | — |
| P. aeruginosa ATCC27853 | 2 | — | — | — | — |
| E. coli ATCC25922 | 2 | — | — | — | — |
| A. baumannii ATCC17978 | 0.5 | — | — | — | — |
| A. baumannii ATCC19606 | 0.25 | — | — | — | — |
| A. baumannii ATCC45530 | 0.5 | — | — | — | — |
| A. baumannii ATCC46709 | 1 | — | — | — | — |
| Gram-positive | | | | | |
| S. aureus ATCC19636 | 2 | ND | ND | ND | ND |

—, not determined;
ND, no detectable antimicrobial activity

Significance of Length or Arginine Content

Given the fact that the terminal cysteine appears to be important for the bactericidal activity, we asked if the total length of the HBcARD 150-177C peptide (28-mer) can be further reduced. We compared the potencies against *S. aureus* among peptides 150-168C (19-mer), 157-176C (20-mer), and 164-177C (14-mer). As shown in Table 4, none of these peptides showed detectable activity. The results here indicated that shortened peptides with a reduced number of arginines exhibited no antimicrobial activity against *S. aureus*. See Table 4. On the other hand, we have shown that shorter peptides containing 3 variable domains are sufficient to kill other bacteria (data not shown).

Figure 5:
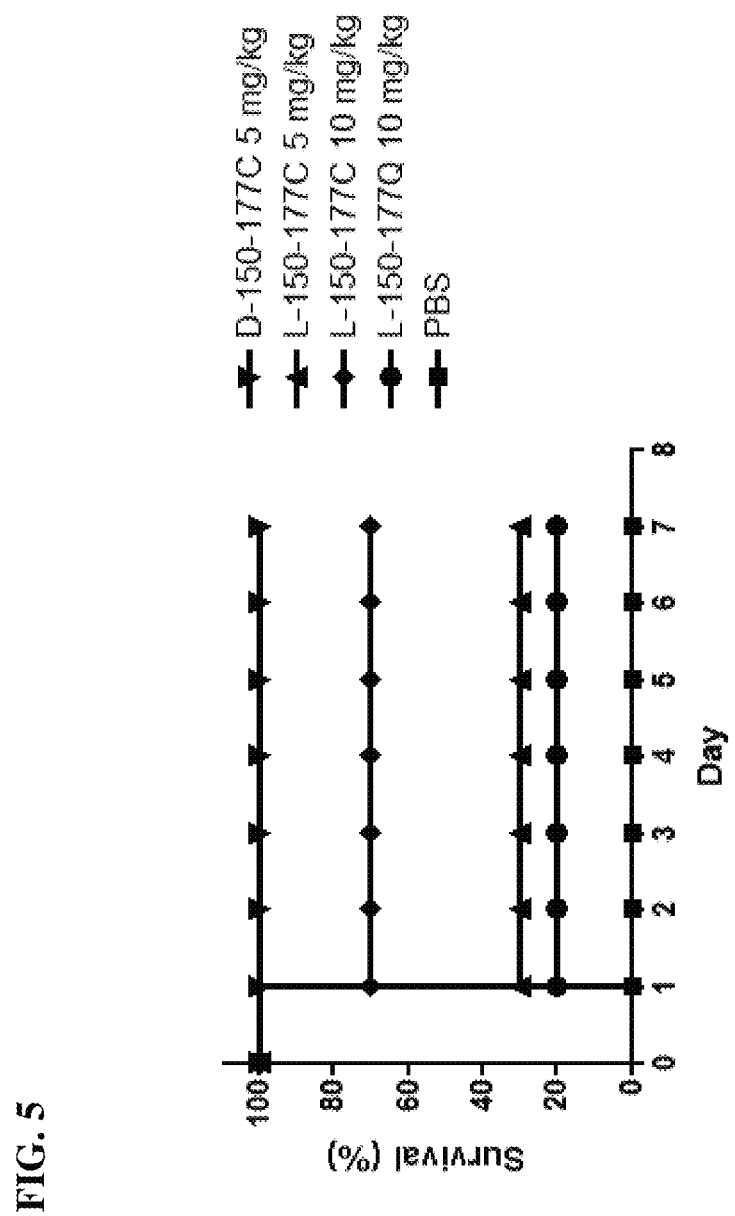
FIG. 5 is a graph showing in vivo protection efficacies of various modified HBcARD peptides at different doses in an ICR mouse sepsis model.

The 28-Mer Peptide D-150-177C Improved Protection Efficacy in a Sepsis Mouse Model We compared the in vivo protection efficacy of HBcARD 150-177C peptides (28-mer) containing either D-form or L-form arginines. See Table 1 and FIG. 5. ICR mice (n=10/group) were ip. inoculated with *S. aureus* ATCC19636 (4×10⁶/mouse), followed by treatment with modified peptides at two hours post-inoculation. All PBS control mice died on day 1, and only 20% of the mice treated with control peptide (150-177Q) survived. Administration of L-150-177C peptide at the dose of 5 and 10 mg/kg protected 30% and 70% mice from death, respectively. See FIG. 5. When treated with 5 mg/kg of D-150-177C, all mice (100%) survived.

The 28-Mer Peptide D-150-177C Protected Mice from Lung Infection with Colistin-Resistant *A. baumannii*

Figure 6:
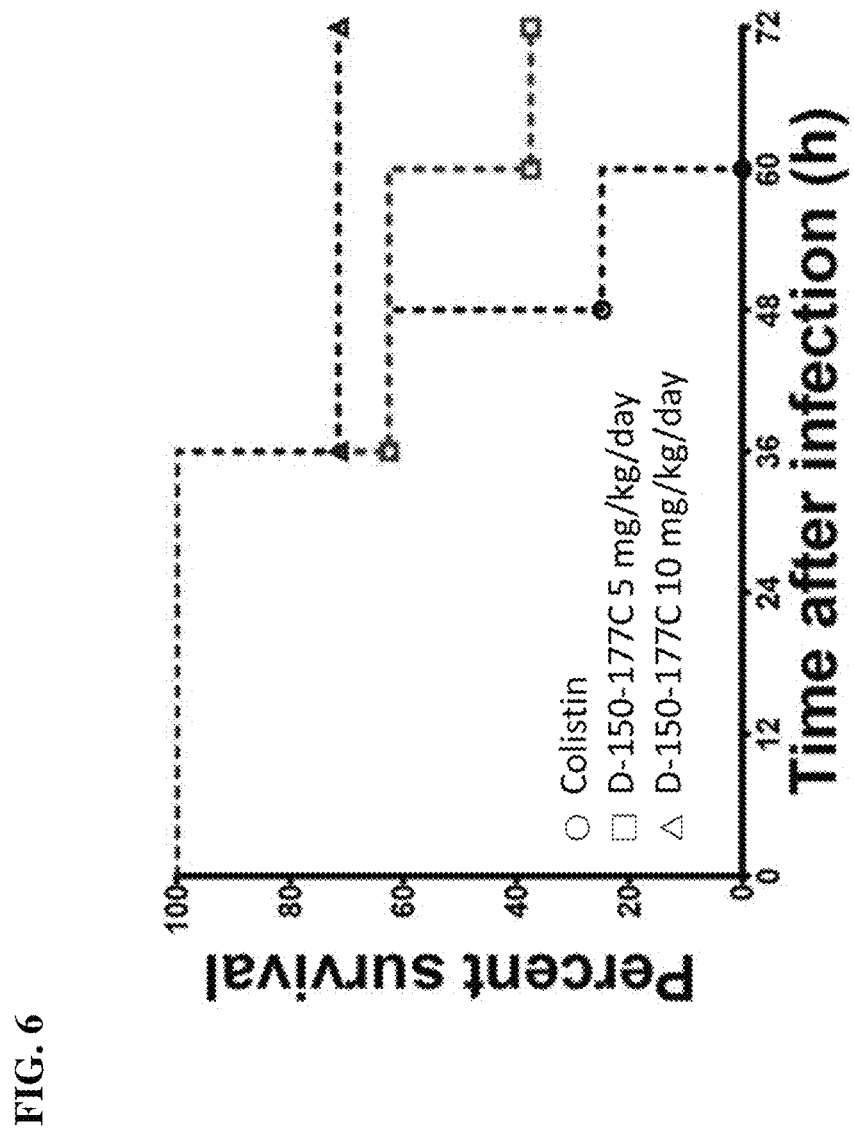
FIG. 6 is a graph showing in vivo protection efficacies of 150-177C and 150-177Q peptides in a BALB/c mouse lung infection model. Colistin-resistant A. baumannii was inoculated via intra-tracheal route.

BALB/c mice (n=8/group) were intra-tracheally inoculated with colistin-resistant *A. baumannii* TCGH 46709 (3.4×10⁸ cfu/mouse). These lung-infected mice were ip. treated with colistin (5 mg/kg/day) or D-150-177C (5 and 10 mg/kg/day), respectively. All mice treated with colistin died at 60 hours post-inoculation with drug-resistant *A. baumannii*. See FIG. 6. In contrast, there was a dose-dependent protection effect from D-150-177C. A significant difference was observed when the mice were treated with 10 mg/kg/day of D-150-177C peptide (p<0.05). See FIG. 6.

Comparison of In Vivo Toxicity Between Peptide D-150-177C and Polymyxin B

Using the sepsis mouse model, we examined the survival rates of ICR mice intraperitoneally (i.p.) injected with the 28-mer D-150-177C peptide (20-80 mg/kg body weight) and polymyxin B (a colistin-related compound) (50 mg/kg body weight). See FIG. 7, A. All mice treated with polymyxin B (50 mg/kg) died at day one, as expected from the notorious nephrotoxicity of colistin and polymyxin B to kidney. See FIG. 7, A. In contrast, no acute toxicity was observed in the mice treated with 20 and 40 mg/kg D-150-177C. See FIG. 7, A. When the doses were increased to 60 and 80 mg/kg, survival rates of mice were decreased to 80% and 40%, respectively. See, FIG. 7, A. Liver injury can be detected by the serum ALT level. Mice treated with D-150-177C in the dose range of 20 to 40 mg/kg showed a higher ALT level than polymyxin B, but the p value is insignificant. See FIG. 7, B. The ALT levels of mice treated with 60 mg/kg were significantly higher than those treated at 20 mg/kg polymyxin B (p<0.01). See FIG. 7, B.

Figure 8:
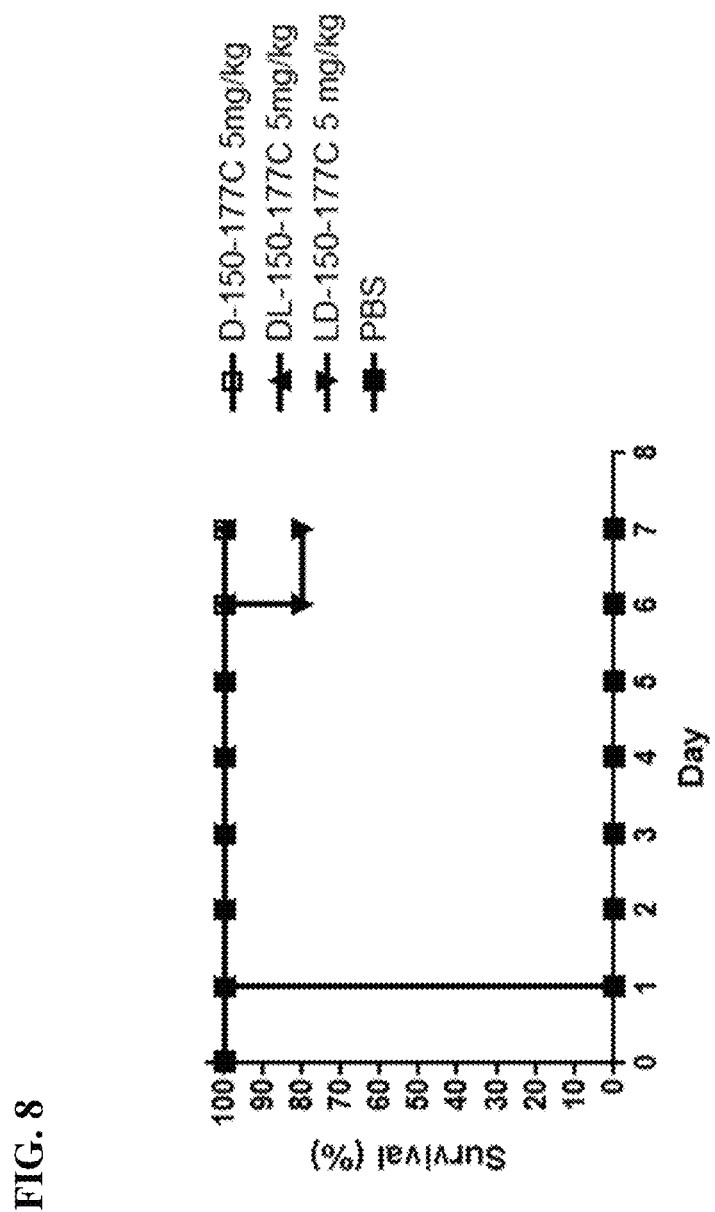
FIG. 8 is a graph showing in vivo protection efficacies of all-D-arginine and partial-D-arginine substituted 150-177C peptides in a mouse sepsis model. Two hours after the inoculation, the mice (n=10/group) were treated with 5 mg/kg of various peptides D-, DL-, LD-150-177C, and PBS, respectively. Peptides D- and DL-150-177C protected all S. aureus-infected mice from death, while peptide LD-150-177C protected only 80% of mice.

Comparison of In Vivo Protection Efficacies Among Various Modified 150-177C Peptides The 28-mer peptide D-150-177C contains a total of 14 L-arginines substituted with 14 D-arginines. See Table 1 and FIG. 6. D-arginine is far more expensive than L-arginine. To reduce the cost of peptide synthesis, we compared the in vivo protection efficacies between peptides containing complete or partial D-arginine substitution. See Table 1 and FIG. 8. Peptide DL-150-177C is only partially D-arginine substituted, and exhibited very similar protection efficacy to all-D-arginine substituted peptide D-150-177C (100% substitution). See FIG. 8. In contrast, the protection efficacy of peptide LD-150-177C (also partially substituted) appeared to be less than DL-150-177C. See FIG. 8.

Serine and Threonine are Dispensable

Figure 9:
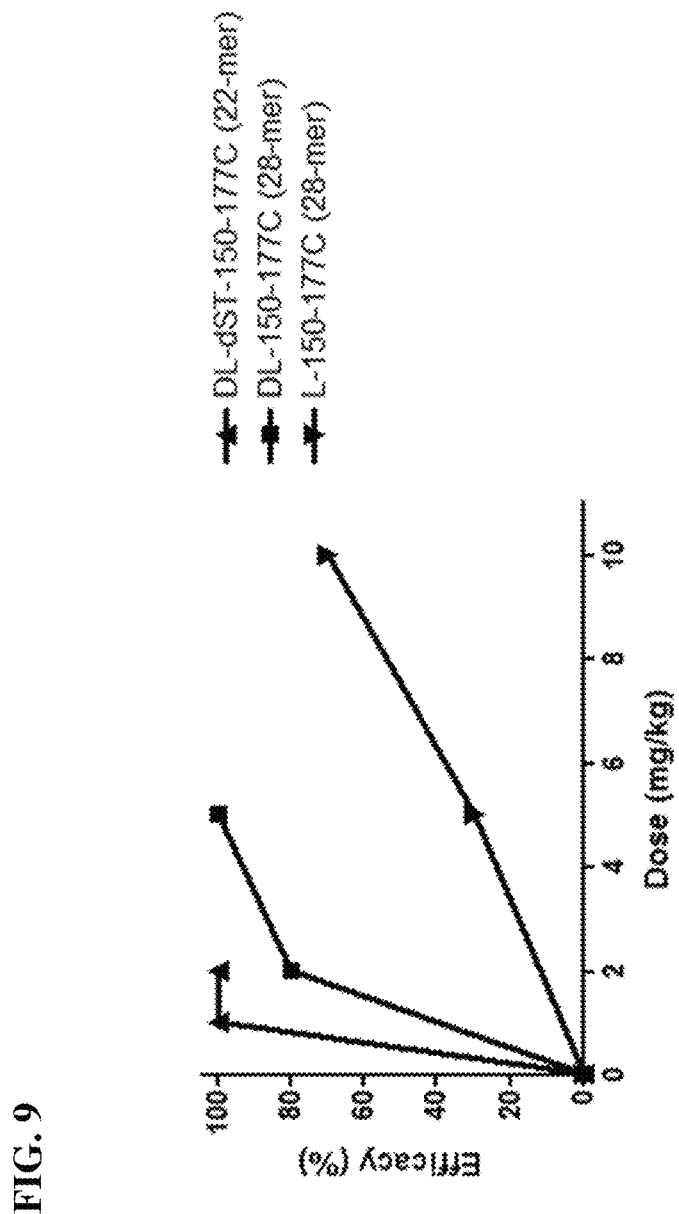
FIG. 9 is a graph showing that deletion of serine and threonine residues from peptide DL-150-177C improved the in vivo protection efficacies at different doses in a mouse sepsis model.

We engineered a new 22-mer peptide, DL-dST-150-177C (see Table 1), with two major modifications: (1) partial-D-arginine substitution by using the backbone of peptide DL-150-177C; and (2) deletion of 5 serine and one threonine residues from the parental 28-mer peptide DL-150-177C. This 22-mer peptide DL-dST-150-177C showed remarkably improved protection efficacy compared to the 28-mers DL-150-177C and L-150-177C. See FIG. 9.

Bacterial Isolates

The antimicrobial activities of HBcARD peptides were tested using a number of bacterial strains, including *Pseudomonas aeruginosa* Migula strains (ATCC 27853, ampicillin-resistant and ATCC 9027, ampicillin-resistant), *Klebsiella pneumoniae* strain (ATCC 13884), *Shigella dysenteriae* Xen27 (Caliper Co.), *Escherichia coli* strain (ATCC 25922), *Staphylococcus aureus* subsp. strains (ATCC 25923, methicillin-resistantATCC 29213, methicillin-resistant and ATCC 19636, methicillin-resistant) and *Acinetobacter baumannii* strains (ATCC 17978, ATCC 17978 CR, ATCC19606, ATCC 19606 CR, TCGH 45530 and TCGH 46709). Clinical isolates TCGH 45530 and TCGH 46709 were obtained from Tzu-Chi Buddhist General Hospital (TCGH) in Taiwan, and were identified using the Vitek system (Biomerieux Vitek, Inc., Hazelwood, MO, USA). See Chang et al. (2012), J Microbiol Immunol Infect 45:37-42 doi:10.1016/j.jmii.2011.09.019.

Antimicrobial Assay

L- and D-HBcARD peptides were purchased from Yao-Hong Biotechnology Inc. (Taipei, Taiwan). Antimicrobial activity was determined as described. See, Chen et al., 2013. Briefly, bacteria were grown in MH broth (Difco) to mid-logarithmic phase at 37° C., and were diluted to $10^6$ CFU (colony formation unit)/ml in phosphate buffer (10 mM sodium phosphate and 50 mM sodium chloride, pH 7.2). Peptides were serially diluted in the same buffer. Fifty microliters (μl) of bacteria were mixed with fifty μl of peptides at varying concentrations, followed by incubation at 37° C. for 3 hours without shaking. At the end of incubation, bacteria were placed on Mueller-Hinton broth agar plates, and allowed to grow at 37° C. overnight for measurement of minimal bactericidal concentration (MBC). The lowest peptide concentration that displayed no bacterial growth (zero colony) was defined as MBC.

All peptides were tested in triplicate.

Stability to Proteases

L- and D-HBcARD peptides (0.5 nmol) were mixed with MBC buffer in the presence or absence of 5% serum collected from bovine, mouse and human origins. After incubation at 37° C. for 3 hours, the amounts of peptides surviving the protease digestion were determined by SDS-PAGE electrophoresis and staining with Green Angel. The images were quantified using image J software and the intensities were normalized with the no serum control. To investigate the effect of serum on the antimicrobial activity of HBcARD peptides, L- and D-HBcARD peptides at their respective MBC concentrations were incubated with *S. aureus* ATCC19636 strain ($10^6$ CFU/ml) at 37° C. for three hours. Bacteria were plated on MH agar and the antimicrobial activity was determined by colony formation.

Hemolytic Activity

The hemolytic activities of peptides were determined by hemolysis against human red blood cells (hRBCs). Human blood was obtained in EDTA-containing tube and was centrifuged at 450 g for 10 min. The pellet was washed three times with PBS buffer, and a solution of 10% hRBCs was prepared. hRBCs solution was mixed with serial dilutions of peptides in PBS buffer, and the reaction mixtures were incubated for 1 h at 37° C. After centrifugation at 450 g for 10 min, the percentage of hemolysis was determined by measuring the absorbance at the wavelength of 405 nm of the supernatant. Blank and 100% hemolysis were determined in PBS buffer and in the presence of 1% Triton X-100, respectively.

In Vivo Animal Studies

Three-week old male ICR mice (19 to 21 g) were purchased from BioLASCO (Taiwan). To test the in vivo protection efficacy of the HBcARD peptides, all mice were inoculated intraperitoneally with *S. aureus* ATCC 19636 ($4 \times 10^6$ CFU/mouse). HBc147-183 (L- or D-HBcARD) or the PBS control was administered intraperitoneally at 2 hours after bacterial inoculation, respectively. Each group contained 10 mice. Mortality was monitored daily for 7 days following the bacterial inoculation.

To investigate the potential immunogenicity of HBcARD peptides, we determined the in vivo antimicrobial activity of HBcARD peptide in peptide-immunized mice. Briefly, three week-old male mice were immunized three times with 0.2 ml of L- and D-HBcARD peptides (5 mg/kg) at day 0, 3, 6, respectively. Immunized mice were inoculated with *S. aureus* ATCC 19636 ($4 \times 10^6$ CFU/mouse) at day 14, and were administered with 0.2 ml of PBS, or L- and D-HBcARD peptide (10 mg/kg) one-hour postinoculation. Another group of mice received the identical protocol with PBS as a control. Each group contained 5 mice. Mortality was monitored daily for 7 days following the bacterial inoculation.

Statistical Analysis

Statistical analysis was performed using Graphpad software. The results were shown in mean±SD, and the difference between individual groups was analyzed by student t test. Survival curves were plotted by Kaplan-Meier method and analyzed by log-rank test.

OTHER EMBODIMENTS

All of the features disclosed in this specification may be combined in any combination. Each feature disclosed in this specification may be replaced by an alternative feature serving the same, equivalent, or similar purpose. Thus, unless explicitly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes, derivatives, and modifications of the embodiments to adapt it to various usages and conditions. Thus, other embodiments are also within the claims.

What is claimed is:

1. An antimicrobial peptide, consisting of RRRGRSPRRRTPSPRRRRSQSPRRRRSC (SEQ ID NO: 7) or RRRGRPRRRPPRRRRQPRRRRC (SEQ ID NO: 9); optionally, at least one of the arginine residues in the peptide is D-arginine.

2. The antimicrobial peptide of claim 1, wherein at least one of the arginine residues is D-arginine.

3. The antimicrobial peptide of claim 2, wherein the peptide consists of rRrGRPrRrPPrRrRQPrRrRC (SEQ ID NO: 9), in which R is L-arginine and r is D-arginine.

4. The antimicrobial peptide of claim 2, wherein the peptide consists of rRrGRSPrRrTPSPrRrRSQSPrRrRSC (SEQ ID NO: 7), in which R is L-arginine and r is D-arginine.

5. The antimicrobial peptide of claim 2, wherein the peptide consists of RrRGRSPrRTPSPRrRrSQSPRrRrSC (SEQ ID NO: 7), in which R is L-arginine and r is D-arginine.

6. The antimicrobial peptide of claim 1, wherein the peptide consists of RRRGRPRRRPPRRRRQPRRRRC (SEQ ID NO: 9), in which each of the arginine residues in the peptide is L-arginine.

7. The antimicrobial peptide of claim 1, wherein the peptide consists of RRRGRSPRRRTPSPRRRRSQSPRRRRSC (SEQ ID NO: 7), in which each of the arginine residues in the peptide is L-arginine.

8. A pharmaceutical composition comprising the antimicrobial peptide of claim 1 and a pharmaceutically acceptable carrier.

9. A method of treating a bacterial infection, the method comprising administering the composition of claim 8 to a subject in need thereof.

10. A chimeric antimicrobial peptide, consisting of RRRGRSPRRRTPSPRRRRSOSPRRRRSC (SEQ ID NO: 7) or RRRGRPRRRPPRRRRQPRRRRC (SEQ ID NO: 9), and an affinity tag, a signal sequence, a ligand, or another antimicrobial peptide or fragment thereof; optionally, at least one of the arginine residues in the peptide is D-arginine.

11. The chimeric antimicrobial peptide of claim 10, wherein the antimicrobial peptide consists of RRRGRPRRRPPRRRRQPRRRRC (SEQ ID NO: 9), in which each of the arginine residues in the peptide is L-arginine or at least one of the arginine residues is D-arginine.

12. The chimeric antimicrobial peptide of claim 11, wherein the antimicrobial peptide consists of rRrGRPrRrPPrRrRQPrRrRC (SEQ ID NO: 9), in which R is L-arginine and r is D-arginine.

13. The chimeric antimicrobial peptide of claim 10, wherein the antimicrobial peptide consists of RRRGRSPRRRTPSPRRRRSQSPRRRRSC (SEQ ID NO: 7), in which each of the arginine residues in the peptide is L-arginine or at least one of the arginine residues is D-arginine.

14. The chimeric antimicrobial peptide of claim 13, wherein the antimicrobial peptide consists of rRrGRSPrRrTPSPrRrRSQSPrRrRSC (SEQ ID NO: 7), in which R is L-arginine and r is D-arginine.

15. The chimeric antimicrobial peptide of claim 13, wherein the antimicrobial peptide consists of RrRGRSPRrRTPSPRrRrSQSPRrRrSC (SEQ ID NO: 7), in which R is L-arginine and r is D-arginine.

16. An antimicrobial peptide conjugate, the conjugate consisting of RRRGRSPRRRTPSPRRRRSQSPRRRRSC (SEQ ID NO: 7) or RRRGRPRRRPPRRRRQPRRRRC (SEQ ID NO: 9), and a non-peptide moiety; optionally, at least one of the arginine residues in the peptide is D-arginine.

17. The antimicrobial peptide conjugate of claim 16, wherein the antimicrobial peptide consists of RRRGRPRRRPPRRRRQPRRRRC (SEQ ID NO: 9), in which each of the arginine residues in the peptide is L-arginine or at least one of the arginine residues is D-arginine.

18. The antimicrobial peptide conjugate of claim 17, wherein the antimicrobial peptide consists of rRrGRPrRrPPrRrRQPrRrRC (SEQ ID NO: 9), in which R is L-arginine and r is D-arginine.

19. The antimicrobial peptide conjugate of claim 16, wherein the antimicrobial peptide consists of RRRGRSPRRRTPSPRRRRSQSPRRRRSC (SEQ ID NO: 7), in which each of the arginine residues in the peptide is L-arginine or at least one of the arginine residues is D-arginine.

20. The antimicrobial peptide conjugate of claim 19, wherein the antimicrobial peptide consists of rRrGRSPrRrTPSPrRrRSQSPrRrRSC (SEQ ID NO: 7), in which R is L-arginine and r is D-arginine.

21. The antimicrobial peptide conjugate of claim 19, wherein the antimicrobial peptide consists of RrRGRSPRrRTPSPRrRrSQSPRrRrSC (SEQ ID NO: 7), in which R is L-arginine and r is D-arginine.

* * * * *